(12) United States Patent
Fukae et al.

(10) Patent No.: US 7,034,180 B2
(45) Date of Patent: Apr. 25, 2006

(54) METHOD FOR CRYSTALLIZATION OF HYDROXYCARBOXYLIC ACIDS

(75) Inventors: Masafumi Fukae, Takasago (JP);
Yoshiro Hiraishi, Himeji (JP)

(73) Assignee: Kaneka Corporation, Osaka (JP)

( * ) Notice: Subject to any disclaimer, the term of this patent is extended or adjusted under 35 U.S.C. 154(b) by 111 days.

(21) Appl. No.: 10/362,460

(22) PCT Filed: Sep. 7, 2001

(86) PCT No.: PCT/JP01/07762

§ 371 (c)(1),
(2), (4) Date: May 8, 2003

(87) PCT Pub. No.: WO02/20453

PCT Pub. Date: Mar. 14, 2002

(65) Prior Publication Data

US 2005/0075508 A1    Apr. 7, 2005

(30) Foreign Application Priority Data

Sep. 7, 2000  (JP) .............................. 2000-271895

(51) Int. Cl.
*C07C 61/12*  (2006.01)
(52) U.S. Cl. ...................... 562/500; 562/580; 562/501; 562/502
(58) Field of Classification Search ................ 562/498, 562/500, 501, 508, 510
See application file for complete search history.

(56) References Cited

U.S. PATENT DOCUMENTS

| 4,361,515 | A | | 11/1982 | Terahara et al. | |
| 4,438,277 | A | * | 3/1984 | Terahara et al. | ............ 560/119 |
| 5,250,435 | A | | 10/1993 | Cover et al. | |

FOREIGN PATENT DOCUMENTS

| EP | 0 033 538 A2 | | 8/1981 |
| EP | 0 486 153 A2 | | 5/1992 |
| GB | 2 073 199 A | | 10/1981 |
| GB | 2073199 | * | 10/1981 |
| HU | P9602060 A | | 1/1994 |
| HU | P9600154 A | | 2/1997 |
| JP | 56-122375 A | | 9/1981 |
| JP | 56-142236 A | | 11/1981 |
| JP | 56-150037 A | | 11/1981 |

* cited by examiner

*Primary Examiner*—Johann Richter
*Assistant Examiner*—Karl Puttlitz
(74) *Attorney, Agent, or Firm*—Foley & Lardner LLP

(57) ABSTRACT

The invention aims at producing high-purity crystals of a hydroxycarboxylic acid represented by the following formula (1):

(1)

in high yield.

Provided are a method for crystallization of a compound (1) which comprises acidifying a mixture of a solution of an alkali salt of the compound (1) and an organic solvent, and a method for crystallization of compound (1) by mixing a solution of the compound (1) in a water-miscible good solvent with water, in which a slurry with a necessary suspension amount of the compound (1) for inhibiting oil formation and scaling is prepared in advance and then a main crystallization is carried out in the presence of said slurry.

19 Claims, No Drawings

METHOD FOR CRYSTALLIZATION OF HYDROXYCARBOXYLIC ACIDS

TECHNICAL FIELD

The present invention relates to a method for crystallization of a compound (1) of the following general formula (1):

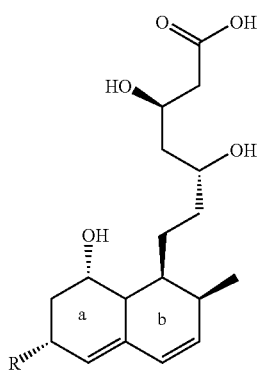
(1)

in which R is $CH_3$, $CH_2OH$, $CH_2OCOR^1$, $CO_2R^2$, $CONR^3R^4$, OH, $CH_2OR^1$ or $CH_2NR^3R^4$; $R^1$ is a $C_{1-5}$ alkyl group; $R^2$ is H or a $C_{1-5}$ alkyl group; $R^3$ and $R^4$ are independently selected from among H and $C_{1-5}$ alkyl groups; a and b each is a double bond, one of a and b is a single bond with the other being a double bond or a and b each is a single bond. The above compound (1) is a quite useful compound as a common intermediate for the production of therapeutic agents for hyperlipemia, particularly a class of highly functional drugs capable of controlling cholesterol biosynthesis by inhibiting HMG-CoA reductase which are represented by the following general formula (3):

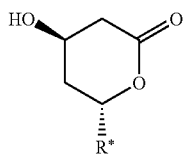
(3)

or the following general formula (4):

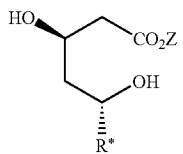
(4)

wherein Z is H, a $C_{1-5}$ alkyl group, or a $C_{1-5}$ alkyl group substituted by a member selected from the group consisting of phenyl, dimethylamino and acetylamino; R* is

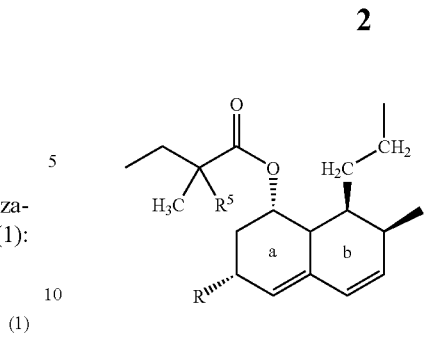

wherein R, a, and b are as defined above; $R^5$ is H or $CH_3$.

BACKGROUND TECHNOLOGY

There is a report on the isolation of said compound (1) as the corresponding ammonium or other salt (Japanese Kokai Publication Hei-6-7176) so far, but there is no knowing of the compound (1) being ever isolated as crystals of simple substance the compound (1). While the compound (1) can be synthesized from a compound (2) represented by the general formula (2);

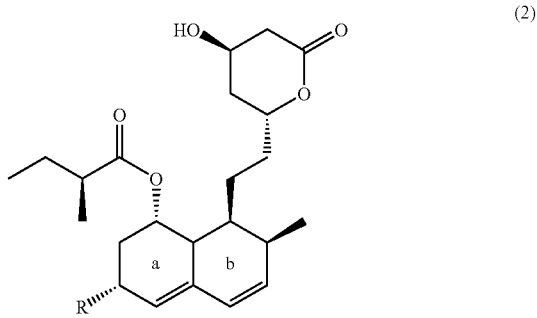
(2)

its isolation has heretofore been made by several alternative methods such as the method which comprises hydrolyzing the side-chain acyl group of compound (2) enzymatically to give a solution thereof (European Patent Publication Number EP0486153A2), the method which comprises alkaline hydrolysis and subsequent extraction with a solvent to give a solution thereof (Japanese Kokai Publication Sho-56-122375), and the method which comprises extracting a culture medium containing compound (1) with a solvent to give an extract solution thereof (Japanese Kokai Publication Hei-6-7176), among others, but what is isolated is invariably a solution.

These prior art methods of obtaining compound (1) presented several problems in commercial application. For example, when the final product is obtained in solution form, it is inevitable that, unless a solvent substitution is carried out, the reaction solvent species which can be used in the next step is restricted to the solvent species used for deacylation or extraction or a mixture solvent containing the same solvent species. Moreover, the product in the form of a solution is inconvenient in handling, e.g. transport and storage, thus having problems in the scope of utility as a universal intermediate. Furthermore, while pharmaceutical intermediates in general are required to be of high quality, the purification technology is self-limited when the substances to be purified are available only in solution form, and although the ion-exchange purification method or the like can be utilized, high-purity products can hardly be obtained by using a multi-purpose equipment at low cost.

Furthermore, although the isolation in the form of an ammonium salt is known according to Japanese Kokai Publication Hei-6-7176, generally the isolation of a salt not only calls for time-consuming solvent substitution with a solvent system which is suited to separation and the presence of a carboxyl group-containing impurity interferes with efficient purification; thus salts of necessity impose a limitation on the solvent species which can be used in the next step, with the result that the method is by no means a commercially recommendable method.

SUMMARY OF INVENTION

As a result of intensive investigations for overcoming the above-mentioned disadvantages, the present inventors could discover a method for crystallization which can be commercially carried out, by which oil formation and scaling can be prevented and the compound (1) can be obtained as good crystals which can be handled with good workability. Based on these findings, they have completed the present invention.

The present invention, therefore, is directed to a method for crystallization of compound (1)
which comprises acidifying a mixture of a solution of an alkali salt of the compound (1) of the general formula (1) and an organic solvent in such a manner that the solubility of the compound (1) at completion of crystallization will be 3 weight % or less.

The present invention is further directed to a method for crystallization of a compound (1)
by mixing a solution of compound (1) in a water-miscible good solvent with water,
in which a slurry with a necessary suspension amount of the compound (1) for inhibiting oil formation and scaling of the compound (1) is prepared in advance and a main crystallization is then carried out in the presence of said slurry.

DISCLOSURE OF INVENTION

The compound for use in the present invention is a compound represented by the following general formula (1).

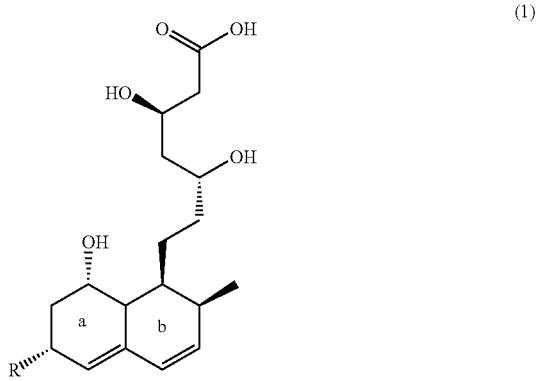

(1)

In the above formula, R represents $CH_3$, $CH_2OH$, $CH_2OCOR^1$, $CO_2R^2$, $CONR^3R^4$, OH, $CH_2OR^1$ or $CH_2NR^3R^4$ ($R^1$ is a $C_{1-5}$ alkyl group, $R^2$ is H or a $C_{1-5}$ alkyl group, $R^3$ and $R^4$ are independently selected from among H and $C_{1-5}$ alkyl groups); a and b each is a double bond, one of a and b is a single bond with the other being a double bond or a and b each is a single bond. From the viewpoint of usefulness as an intermediate of antihyperlipemic agents, it is preferable that R be $CH_3$ or OH, particularly $CH_3$, and that a and b each be a double bond.

The above-mentioned solution of compound (1) or a salt thereof can be generally prepared by a suitable procedure such as extraction or solvent substitution of the solution which was obtained in a deacylation reaction of the side-chain acyl group of compound (2) or in a process of culture or the like.

The above-mentioned suitable procedure includes, for example, the procedure described in Japanese Kokai Publication Hei-6-7176 wherein the compound (1) obtained as a product in culture is extracted in the acid form with isopropyl acetate at pH 4 to 4.5 and back-extracted into an aqueous solution of sodium carbonate at pH 11.5 to give an aqueous solution of the sodium salt of compound (1) and the procedure in which the above aqueous solution is further readjusted to pH 4 with phosphoric acid and then extracted with isopropyl acetate to give a solution of compound (1) in isopropyl acetate.

Furthermore, referring to the method which comprises deacylating the side-chain acyl group of compound (2) to give a solution of compound (1), an example is described in which the compound (2) is deacylated with lithium hydroxide and then acidified with phosphoric acid and the reaction product is extracted with ethyl acetate to give the objective solution (Japanese Kokai Publication Sho-56-122375).

Regarding the method for crystallization of the compound (1), the method for crystallization by acidification of a solution of an alkali salt of compound (1) is first described.

The alkali salt of compound (1) for use in this method for crystallization is not particularly restricted but is preferably an alkali metal salt or an amine salt, including specifically the lithium salt, sodium salt, potassium salt, ammonium salt, pyridinium salt, trimethylamine salt, triethylamine salt, and so on.

In this method for crystallization, the crystallization is effected by acidifying a solution of an alkali salt of compound (1) in the concomitant presence of an organic solvent in such a manner that the solubility of compound (1) at completion of crystallization will be 3 weight % or less. In order that the crystallization may be suitably conducted, it is important to have an organic solvent present concomitantly at the time of acidification.

The above-mentioned solubility can be determined by the absolute calibration method using a reference standard with the high performance liquid chromatography. The measurement conditions are described below.

Column: ODS column, Nacalai Tesque, Inc. Cosmosil 5C18-AR-300

Eluent: acetonitrile/0.1% aqueous solution of phosphoric acid (pH 4.2)=50/100 (v/v)

Flow rate: 1.5 ml/min

Detection: 238 nm (UV detector)

Temperature: 35° C.

The organic solvent to be concomitantly present is not particularly restricted but is preferably selected from among hydrocarbons, ethers, esters, ketones, halogenated hydrocarbons, nitriles, and alcohols. Among these, $C_{5-12}$ saturated hydrocarbons represented by $C_nH_{2n+2}$ or $C_nH_{2n}$, $C_{5-12}$ unsaturaed hydrocarbons represented by $C_nH_{2n}$, or $C_nH_{2n-2}$, $C_{6-12}$ aromatic hydrocarbons, $C_{4-10}$ ethers, $C_{3-10}$ esters, $C_{3-10}$ ketones, $C_{1-8}$ halogenated hydrocarbons, $C_{2-6}$ nitriles, and $C_{1-8}$ alcohols are more preferred, $C_{6-12}$ aromatic hydrocarbons are still more preferred.

Specifically, the $C_{5-12}$ saturated hydrocarbons represented by $C_nH_{2n+2}$ or $C_nH_{2n}$ include pentane, n-hexane, iso-hexane, n-heptane, octane, methylcyclohexane and ethylcyclohexane; the $C_{5-12}$ unsaturated hydrocarbons represented by $C_nH_{2n}$ or $C_nH_{2n-2}$ include 1-hexene; the $C_{6-12}$ aromatic hydrocarbons include benzene, toluene, xylene and ethylbenzene; the $C_{4-10}$ ethers include tetrahydrofuran, 1,4-dioxane and tert-butyl methyl ether; the $C_{3-10}$ esters include ethyl acetate, isopropyl acetate and butyl acetate; the $C_{3-10}$ ketones include acetone, methyl ethyl ketone, methyl isobutyl ketone and cyclohexanone; the $C_{1-8}$ halogenated hydrocarbons include dichloromethane, 1,2-dichloroethane; the $C_{2-6}$ nitriles include acetonitrile; and the $C_{1-8}$ alcohols include methanol, ethanol, 1-propanol, 2-propanol, 1-butanol, tert-butanol, 1-hexanol and 2-hexanol.

The preferred are pentane, n-hexane, iso-hexane, n-heptane, octane, methylcyclohexane, benzene, toluene, xylene, tert-butyl methyl ether, ethyl acetate, acetone, methyl isobutyl ketone, dichloromethane, acetonitrile and 2-propanol. More preferred are benzene, toluene, and xylene.

These solvents can be used each independently or as a mixture of two or more species. And needless to say, solvents other than those mentioned above may be present within the range not exerting an adverse effect.

The amount of the organic solvent to be concomitantly present depends on the kind of organic solvent and the concentration of compound (1), and from productivity and other points of view its weight ratio to the solution of an alkali salt of compound (1) is preferably 0.05 to 10, more preferably 0.2 to 4.

Specifically, when a hydrocarbon such as hexane or an aromatic hydrocarbon such as toluene is used as the concomitant solvent, its weight ratio to the solution of an alkali salt of compound (1) is preferably 0.1 to 10, more preferably 0.2 to 4. Similarly when an ester such as ethyl acetate, a ketone such as methyl isobutyl ketone, or an alcohol such as 2-propanol is used as the concomitant solvent, its weight ratio to the solution of an alkali salt of compound (1) is preferably 0.05 to 2, more preferably 0.1 to 0.5.

While, in the present method for crystallization, the solution of an alkali salt of compound (1) is acidified in the concomitant presence of above organic solvent, this acidification is usually effected by adding an acid to said alkali salt solution from the viewpoint of handling. The acid which can be added includes various acids only provided that the pH may be finally adjusted to pH 6 or less, preferably 5 or less, thus including inorganic acids such as sulfuric acid, hydrochloric acid, phosphoric acid and perchloric acid; carboxylic acids such as formic acid, trifluoroacetic acid and trichloroacetic acid; and sulfonic acids such as p-toluenesulfonic acid and methanesulfonic acid; and so on. From commercial points of view, however, inexpensive inorganic acids are preferred and sulfuric acid is suitable among these.

The addition of above-mentioned acid may be made over about 5 minutes to about 10 hours but in order to obtain large-particle sized crystals with good workability in filtration and the like, the addition should be made usually over not less than 10 minutes, preferably not less than 30 minutes.

The above-mentioned acidification temperature is not particularly restricted provided that the compound (1) may remain stable and that the solubility of compound (1) in the whole system at completion of crystallization will not be more than 3 weight %. However, in consideration of the readiness of compound (1) to undergo cyclization to form a lactone, the stability of compound (1) and the like under high-temperature acidic conditions, the preferred temperature is usually not higher than 70° C. at pH 6 or below, more preferably 0 to 60° C. under the acidic condition up to pH 5.

The solution of an alkali salt of compound (1) for use in the present method for crystallization is either the reaction mixture resulting from the deacylation reaction of compound (2) represented by the general formula (2), or a solution obtained by concentration or solvent substitution of the reaction mixture or by an after-treatment such as adjusting the pH to about 8, for instance. For example, when the deacylation of compound (2) is carried out using an alkali metal hydroxide, the reaction solvent is not particularly restricted provided that it is stable during the deacylation reaction and usually an alcohol, an ether, water, or a mixture thereof can be preferably used. Specifically, alcohols such as ethanol, 2-propanol, tert-butanol; ethers such as 1,4-dioxane; and water can generally be used preferably. Among these, secondary and tertiary alcohols such as 2-propanol and tert-butanol are preferred.

The solvent species for crystallization and the solvent species for above deacylation reaction need not be the same and, after said deacylation reaction, the reaction solvent may be replaced with a solvent suitable for crystallization. When, for example, an alcohol such as 2-propanol is used for the deacylation reaction and potassium hydroxide is used as the alkali, the reaction solvent can be replaced with water by carrying out one or more cycles of concentration and dilution with water after the reaction and the resulting aqueous solution of the potassium salt of compound (1) be used preferably. When necessary, the reaction solvent with the excess potassium hydroxide neutralized to a suitable pH (e.g. pH 8) in advance may be used.

In conducting the present method for crystallization, in order to obtain high quality crystals of compound (1), it is preferable to remove the impurity and color component formed in said deacylation reaction as a byproduct by a treatment with an adsorbent (preferably activated carbon) or the like or, in the case of an aqueous solution, by adjusting the system to a suitable pH and, then, extracting it with a solvent (e.g. adjustment to pH 7.5 and subsequent extraction with ethyl acetate for purification).

The present method for crystallization can be also used as a process for isolation and purification of compound (1) from the reaction mixture or a process for recrystallization of compound (1).

Now, the method for crystallization by mixing a solution of said compound (1) in a water-miscible good solvent with water is described.

The water-miscible good solvent for use in this method is not particularly restricted but is preferably selected from among $C_{1-6}$ saturated alcohols represented by $C_nH_{2n+2}O$, $C_{1-8}$ saturated diols represented by $C_nH_{2n+2}O_2$, $C_{1-8}$ saturated triols represented by $C_nH_{2n+2}O_3$, $C_{3-5}$ ketones represented by $C_nH_{2n}O$, ethers, and nitriles. Among these, said alcohols, ketones, and nitrites are preferred.

Specifically, methanol, ethanol, 1-propanol, 2-propanol, butanol, 2-butanol, 2-methylpropanol, tert-butanol, 2-methylbutanol, 1,2-ethanediol, 1,3-propanediol, 1,5-pentanediol, acetone, methyl ethyl ketone, tetrahydrofuran, 1,4-dioxane, 1,2-dimethoxyethane, acetonitrile, and the like are preferred; methanol, ethanol, 1-propanol, 2-propanol, acetone, and acetonitrile are more preferred; and methanol, 2-propanol, acetone, and acetonitrile are still more preferred.

These solvents can be used each independently or as a mixture of two or more species. And needless to say, solvents other than those mentioned above may be present within the range not exerting an adverse effect.

The mixing of a solution of compound (1) in a water-miscible good solvent with water may be carried out either by adding water to the solution of the compound (1) in a water-miscible good solvent or by adding the solution of the compound (1) in a water-miscible good solvent to water. From the viewpoint of the quality, the particle size and the like property of obtained crystals, the method which comprises adding water to the solution of the compound (1) in a water-miscible good solvent is more preferred.

The present method for crystallization is characterized in that a necessary suspension amount of a slurry for inhibiting oil formation, scaling, preventing difficulty in stirring and the like during crystallization is prepared in advance and a main crystallization is carried out in the presence of said slurry. The slurry which is to be thus formed in advance can be prepared by carrying out a preliminary crystallization or adding crystals of compound (1).

The suspension amount relative to the total amount of compound (1) at completion of main crystallization, which is necessary for inhibiting oil formation, scaling, preventing stirring difficulty and the like during crystallization is usually not less than 1% by weight, preferably 5 to 20% by weight when water is added to a solution of compound (1) in a water-miscible good solvent, or 1 to 5% by weight when a solution of compound (1) in a water-miscible good solvent is added to water. The term "suspension amount" as used herein means the percentage weight of crystals separating out in the whole slurry based on the total weight of compound (1).

There is no particular upper limit to said suspension amount but from economic considerations, the usual upper limit is preferably 30% by weight, more preferably 20% by weight, based on the total amount of compound (1).

The preliminary crystallization for preparing a slurry in advance is now explained. When water is added to a solution of compound (1) in a water-miscible good solvent, it is preferred to cause nucleation for preliminary crystallization by adjusting the mixture composition comprised of the water-miscible good solvent and water to a composition conducive to partial separation of compound (1). When a solution of compound (1) in a water-miscible good solvent is added to water, it is preferred to cause nucleation for preliminary crystallization by adding a portion of the solution in a water-miscible good solvent.

In the preliminary crystallization procedure, the preferred mixture composition for achieving the above-mentioned suspension amount depends on the crystallization system concentration and the kind of solvent used and cannot be stated in general terms. The weight ratio of the water-miscible good solvent to water is, however, preferably 0.1 to 20, more preferably 0.1 to 10, still more preferably 0.3 to 8, in the case where water is to be added to a solution of compound (1) in a water-miscible good solvent. In the case where a solution of compound (1) in a water-miscible good solvent is to be added to water, the ratio referred to above is preferably not more than 1, more preferably not more than 0.5, the lower limit in this case being generally 0.001.

Specifically, when 2-propanol, acetonitrile, or acetone, for instance, is to be used as the water-miscible good solvent, the weight ratio of the water-miscible good solvent to water is preferably 0.1 to 6, more preferably 0.2 to 5, in the case where water is added to a solution of compound (1) in the water-miscible good solvent. On the other hand, when a solution of compound (1) in the water-miscible good solvent is to be added to water, the ratio referred to above is preferably not more than 0.5, more preferably 0.001 to 0.2. When methanol or ethanol, for instance, is used as said water-miscible good solvent, the ratio referred to above is preferably 0.3 to 20, more preferably 0.3 to 15, in the case where water is added to a solution of compound (1) in the water-miscible good solvent, or preferably not more than 1, more preferably 0.001 to 0.5 in the case where a solution of compound (1) in the water-miscible good solvent is added to water.

In order that good nucleation and crystal growth may be attained in this preliminary crystallization, it is generally preferable to carry out preliminary crystallization in such a manner that no abrupt separation of crystals will take place. The preferable procedure for attaining this result is such that, in the case where water is to be added to a solution of compound (1) in a water-miscible good solvent, water is added continuously or portionwise, or in the case where a solution of compound (1) in a water-miscible good solvent is to be added to water, a portion of the solution in a water-miscible good solvent is added continuously or portionwise. The above continuous or portionwise addition is carried out generally over not less than 10 minutes, for instance, but needs usually over not less than 30 minutes, preferably over about 1 hour for obtaining good nucleation and crystal growth. In the mode where a solution of compound (1) in a water-miscible good solvent is added to water, as compared with in the mode in which water is added to a solution of compound (1) in a water-miscible good solvent, the difficulty in stirring, scaling, etc. tend to be suppressed even when the duration of addition is somewhat shorter.

The preliminary crystallization temperature is preferably not higher than 70° C. in consideration of the stability of compound (1) and the like such as the readiness of compound (1) to lactonize at high temperature. The above temperature is more preferably 0 to 50° C. in order that the effect of the invention may be maximized, and still more preferably 0 to 40° C. for obtaining large-particle sized crystals with good reproducibility.

The incubation time for preliminary crystallization is not particularly restricted but it is usually sufficient to incubate the system for not less than about 30 minutes following addition of the predetermined amount of water or the solution of compound (1) in a water-miscible good solvent.

An alternative method for preparing a slurry of said suspension amount in advance is a method which comprises adding crystals of compound (1). When this method is used, in the mode where a solution of compound (1) in a water-miscible good solvent is to be added to water, it is usually preferable to add crystals of compound (1) to the water. In the mode where water is to be added to a solution of compound (1) in a water-miscible good solvent, it is usually preferable to add crystals of compound (1) to a mixture prepared with a predetermined amount of water. The solvent composition, that is to say the weight ratio of the water-miscible good solvent to water, in this case depends on the crystallization system concentration and the kind of solvent used and cannot be stated in general terms but is preferably 0.1 to 20, more preferably 0.3 to 10.

In the method for crystallization by mixing the water-miscible good solvent with water according to the invention, a slurry of said suspension amount is first prepared and a main crystallization is carried out in the presence of said slurry.

The main crystallization is carried out in such a manner that, in the mode where water is added to a solution of compound (1) in a water-miscible good solvent, a predetermined amount of water is added to said slurry or in the mode where a solution of compound (1) in a water-miscible good solvent is added to water, the solution of compound (1) in the water-miscible good solvent is added to said slurry to bring the final water-miscible good solvent-to-water ratio to the necessary ratio to cause precipitation of not less than 80 weight % of the total amount of compound (1), whereby quality crystals of compound (1) can be obtained at a good recovery rate.

The ratio of the water-miscible good solvent to water at completion of main crystallization depends on the combinatin of the water-miscible good solvent and water to be used and the concentration of compound (1) in the water-miscible good solvent but, from productivity points of view, the weight ratio of the water-miscible good solvent to water is preferably 0.01 to 2, more preferably 0.05 to 1.

Specifically, when acetonitrile is used as the water-miscible good solvent, the weight ratio of the water-miscible good solvent to water is preferably 0.01 to 1, more preferably 0.05 to 0.7. By the same token, when methanol or ethanol, for instance, is used as the water-miscible good solvent, the weight ratio of this water-miscible good solvent to water is preferably 0.01 to 3, more preferably 0.05 to 1.

The addition of water or a solution of compound (1) in the water-miscible good solvent in the main crystallization is preferably carried out over at least 10 minutes, and for the purpose of obtaining large-particle sized crystals, the addition is made usually over not less than 30 minutes, preferably over not less than an hour. In the mode where a solution of compound (1) in a water-miscible good solvent is added to water, as compared with in the mode in which water is added to a solution of compound (1) in a water-miscible good solvent, the stirring difficulty, scaling, etc. tend to be suppressed even when the duration of addition is somewhat shorter.

The main crystallization temperature is preferably not higher than 70° C. and, at the start of main crystallization, is more preferably not higher than 60° C., still more preferably not higher than 30° C.

The incubation time for main crystallization is not particularly restricted but it is sufficient to incubate the system for not less than 30 minutes following addition of water or a solution of compound (1) in a water-miscible good solvent.

The method which, instead of conducting a preliminary crystallization under the above-described conditions, comprises adding a total predetermined amount of water to the total amount of a solution of compound (1) in a water-miscible good solvent gradually over a long time or adding the total amount of a solution of compound (1) in a water-miscible good solvent to a predetermined amount of water gradually over a long time to thereby adjust the ratio of the water-miscible good solvent to water at completion of main crystallization to the above-mentioned preferred range may be regarded as a continuous process consisting of preliminary crystallization and main crystallization and can be expected to produce the same result as that obtainable by the method including a preliminary crystallization.

The preferred mode of practicing the present method for crystallization comprises adjusting the weight ratio of the water-miscible good solvent and water to the predetermined ratio, cooling the system further to an internal temperature not higher than 30° C., more preferably 0 to 25° C. before harvesting the crystal crop, so as to insure sufficient separation of crystals. This cooling session leads to a further improvement in the recovery rate of crystals.

The solution of compound (1) in a water-miscible good solvent for use in the present method for crystallization may be a solution of isolated compound (1) dissolved in the corresponding water-miscible good solvent or a solution prepared by neutralizing the reaction mixture resulting from deacylation of compound (2) represented by general formula (2) and removing the separated salt etc. by filtration. In preparing the objective solution from the deacylation reaction mixture, for instance, in the case where 2-propanol is used as the solvent of the deacylation reaction mixture and potassium hydroxide is used as the alkali, a solution prepared by the procedure comprising acidifying the deacylation reaction mixture to pH 3 with a 55% aqueous solution of sulfuric acid, removing a salt such as the separated potassium sulfate by filtration, and adjusting the concentration of compound (1) can be used as the solution in a water-miscible good solvent.

In conducting the present method for crystallization, in order to obtain quality crystals of compound (1), it is preferable to remove the impurity and color component from the solution of a water-miscible good solvent with an adsorbent (preferably activated carbon) in advance.

The crystals obtained by such methods for crystallization can be isolated by a common solid-liquid separation technique such as centrifugation, pressure filtration and suction filtration, preferably followed by washing with a wash solvent of the same composition as that at the completion of crystallization, optionally further followed by drying such as atmospheric pressure drying or drying under reduced pressure (drying in vacuo).

BEST MODE FOR CARRYING OUT THE INVENTION

The following examples illustrate the present invention in further detail. They are, however, by no means limitative of the scope of the present invention. It is to be understood that in the following examples, the identification or assay of compound (1) or a salt thereof was made by the high performance liquid chromatography under the following conditions.

Column: ODS column, Nacalai Tesque, Inc. Cosmosil 5C18-AR-300
Eluent: acetonitrile/0.1% aqueous solution of phosphoric acid (pH 4.2)=50/100 (v/v)
Flow rate: 1.5 ml/min
Detection: 238 nm (UV detector)
Temperature: 35° C.

REFERENCE EXAMPLE 1

Preparation of a Solution of Potassium Salt of 7-[1,2,6,7,8,8a(R)-hexahydro-2(S),6(R)-dimethyl-8(S)-hydroxy-1(S)-naphthyl]-3(R),5(R)-dihydroxyheptanoic acid In 100 ml of 2-propanol was suspended 16.6 g of 6(R)-[2-[8(S)-(2-methylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (hereinafter referred to briefly as lovastatin) (purity 97%, 0.04 mol), which corresponds to the general formula (2) wherein R is $CH_3$ and a and b each is a double bond, followed by addition of 15.84 g of potassium hydroxide (85% purity, 0.24 mol) under stirring. The mixture was heated to 80° C. and reacted. After 6 hours of reaction, a portion of the reaction mixture was subjected to analysis by high performance liquid chromatography. On confirmation that the percent residue of the starting compound lovastatin was not over 0.5%, the reaction system was cooled to room temperature. The reaction mixture was concentrated under reduced pressure to distill off 2-propanol and the same quantity of deionized water as the 2-propanol distilled off was added. This procedure was repeated twice to give an alkaline aqueous solution containing 6 weight % of potassium salt of 7-[1,2,6,7,8,8a(R)-hexahydro-2(S),6(R)-dimethyl-8(S)-hydroxy-1(S)-naphthyl]-3(R),5(R)-dihydroxyheptanoic acid (hereinafter referred to briefly as TOA).

EXAMPLE 1

To 100 g of an aqueous solution of TOA (containing 6 g of TOA) obtained by the same procedure as Reference Example 1 was added 55% sulfuric acid under stirring to adjust the solution to pH 8, followed by addition of 17 g of toluene. While the solution was stirred at room temperature, it was adjusted to pH 3.0 with 10% sulfuric acid (sulfuric acid was added over 1 hour). The mixture was further stirred at pH 3 for 30 minutes, at the end of which time the TOA crystals which had separated out were harvested by suction filtration with Nutsche (the TOA concentration of the whole filtrate was not more than 0.2 weight %). The crystals were washed with water and toluene, respectively, and dried in a vacuo at 40° C. overnight. Analysis by high performance liquid chromatography revealed that the purity and rate of recovery of the crystal crop were 96% and 92%, respectively.

EXAMPLE 2

To 100 g of an aqueous solution of TOA (containing 6 g of TOA) obtained by the same procedure as Reference Example 1 was added 55% sulfuric acid under stirring to adjust the solution to pH 8, followed by addition of 100 g of toluene. While the solution was stirred at room temperature, it was adjusted to pH 3.0 with 10% sulfuric acid (sulfuric acid was added over 1 hour). The mixture was further stirred at pH 3 for 30 minutes, at the end of which time the TOA crystals which had separated out were harvested by suction filtration with Nutsche (the TOA concentration of the whole filtrate was not more than 0.2 weight %). The crystals were washed with water and toluene, respectively, and dried in a vacuo at 40° C. overnight. Analysis by high performance liquid chromatography revealed that the purity and rate of recovery of the crystal crop were 99% and 86%, respectively.

EXAMPLE 3

To 100 g of an aqueous solution of TOA (containing 6 g of TOA) obtained by the same procedure as Reference Example 1 was added 55% sulfuric acid under stirring to adjust the solution to pH 8, followed by addition of 25 g of toluene. While the solution was stirred at 55° C., it was adjusted to pH 3.0 with 10% sulfuric acid (sulfuric acid was added over 1 hour). The mixture was further stirred at pH 3 for 30 minutes, at the end of which time the TOA crystals which had separated out were harvested by suction filtration with Nutsche (the TOA concentration of the whole filtrate was 0.4 weight %). The crystals were washed with water and toluene, respectively, and dried in a vacuo at 40° C. overnight. Analysis by high performance liquid chromatography revealed that the purity and rate of recovery of the crystal crop were 99% and 83%, respectively.

EXAMPLE 4

To 100 g of an aqueous solution of TOA (containing 6 g of TOA) obtained by the same procedure as Reference Example 1 was added 55% sulfuric acid under stirring to adjust the solution to pH 8, followed by addition of 25 g of toluene. While the solution was stirred at 5° C., it was adjusted to pH 2.9 with 10% sulfuric acid (sulfuric acid was added over 1 hour). The mixture was further stirred at pH 2.9 for 30 minutes, at the end of which time the TOA crystals which had separated out were harvested by suction filtration with Nutsche (the TOA concentration of the whole filtrate was not more than 0.2 weight %). The crystals were washed with water and toluene, respectively, and dried in a vacuo at 40° C. overnight. Analysis by high performance liquid chromatography revealed that the purity and rate of recovery of the crystal crop were 98% and 96%, respectively.

EXAMPLE 5

To 100 g of an aqueous solution of TOA (containing 6 g of TOA) obtained by the same procedure as Reference Example 1 was added 55% sulfuric acid under stirring to adjust the solution to pH 8, followed by addition of 17 g of toluene. While the solution was stirred at room temperature, it was adjusted to pH 5.0 with 10% sulfuric acid (sulfuric acid was added over 1 hour). The mixture was further stirred at pH 5 for 30 minutes, at the end of which time the TOA crystals which had separated out were harvested by suction filtration with Nutsche (the TOA concentration of the whole filtrate was 0.2 weight %). The crystals were washed with water and toluene, respectively, and dried in a vacuo at 40° C. overnight. Analysis by high performance liquid chromatography revealed that the purity and rate of recovery of the crystal crop were 98% and 88%, respectively.

EXAMPLE 6

To 100 g of an aqueous solution of TOA (containing 4 g of TOA) obtained by the same procedure as Reference Example 1 was added 55% sulfuric acid under stirring to adjust the solution to pH 8, followed by addition of 25 g of heptane. While the solution was stirred at room temperature, it was adjusted to pH 3.0 with 10% sulfuric acid (sulfuric acid was added over 1 hour). The mixture was further stirred at pH 3 for 30 minutes, at the end of which time the TOA crystals which had separated out were harvested by suction filtration with Nutsche (the TOA concentration of the whole filtrate was not more than 0.2 weight %). The crystals were washed with water and toluene, respectively, and dried in a vacuo at 40° C. overnight. Analysis by high performance liquid chromatography revealed that the purity and rate of recovery of the crystal crop were 95% and 97%, respectively.

EXAMPLE 7

To 100 g of an aqueous solution of TOA (containing 4 g of TOA) obtained by the same procedure as Reference Example 1 was added 55% sulfuric acid under stirring to adjust the solution to pH 8, followed by addition of 25 g of ethyl acetate. While the solution was stirred at room temperature, it was adjusted to pH 3.0 with 10% sulfuric acid (sulfuric acid was added over 1 hour). The mixture was further stirred at pH 3 for 30 minutes, at the end of which time the TOA crystals which had separated out were harvested by suction filtration with Nutsche (the TOA concentration of the whole filtrate was 0.6 weight %). The crystals were washed with water and toluene, respectively, and dried in a vacuo at 40° C. overnight. Analysis by high performance liquid chromatography revealed that the purity and rate of recovery of the crystal crop were 99% and 68%, respectively.

EXAMPLE 8

The deacylation reaction mixture obtained by the same reaction procedure as described in Reference Example 1 was cooled to room temperature and adjusted to pH about 10 with 55% sulfuric acid. The potassium sulfate separating out was parted by suction filtration with Nutsche, followed by washing with a small quantity of 2-propanol. The solution thus obtained was subjected to solvent substitution with water under reduced pressure as in Reference Example 1 to give an aqueous solution containing 6 weight % of TOA. A 40 g portion of this aqueous solution (containing 2.4 g of TOA) was adjusted to pH 8 with 55% sulfuric acid under stirring, followed by addition of 8 g of 2-propanol. Then, under stirring at room temperature, the solution was adjusted to pH 3.0 with 10% sulfuric acid (sulfuric acid was added over 1 hour). The mixture was further stirred at pH 3 for 30 minutes, at the end of which time the TOA crystals which had separated out were harvested by suction filtration with Nutsche (the TOA concentration of the whole filtrate was 1.0 weight %). The crystals were washed with a 20 weight % aqueous solution of 2-propanol and dried in vacuo at 40° C. overnight. Analysis by high performance liquid chromatography revealed that the purity and rate of recovery of the crystal crop were 80% and 81%, respectively.

EXAMPLE 9

In 40 g of methanol at room temperature was dissolved 10 g of a dry TOA crystal (purity 94%) obtained by the same procedure as Example 1. Under stirring at 25° C., 3 g of water was added over a quarter of one hour for preliminary crystallization. The system was further stirred at the same temperature for about 30 minutes to confirm the improvement of stirring the deposited slurry (the amount of the deposited slurry obtained by preliminary crystallization was 12% and the weight ratio of methanol to water was 13.3). For main crystallization, 35 g of water was further added over 2 hours at the same temperature. The mixture was stirred at the same temperature for 30 minutes, at the end of which time the TOA crystals which had separated out were harvested by filtration with Nutsche under reduced pressure and washed with a small quantity of 50% aqueous solution of methanol (the weight ratio of methanol to water at completion of main crystallization was 1.05). The harvested crystal crop was dried in vacuo at 40° C. overnight. Analysis by high performance liquid chromatography revealed that the purity and rate of recovery of the crystal crop were 99.2% and 87%, respectively.

EXAMPLE 10

In 40 g of 2-propanol was dissolved 10 g of a dry TOA crystal (purity 94%) obtained by the same procedure as Example 1, followed by addition of 10 g of water. Then, at 25° C., 0.1 g of TOA crystals (purity 99%) obtained by the same procedure as Example 8 was added and the mixture was stirred for 1 hour for preliminary crystallization. The system was stirred at the same temperature for about 30 minutes to confirm the good facility of stirring the deposited slurry (the amount of the deposited slurry obtained by preliminary crystallization was 4% and the weight ratio of 2-propanol to water was 4.0). For main crystallization, 83 g of water was added over 2 hours at the same temperature. The mixture was stirred at the same temperature for 30 minutes, at the end of which time the TOA crystals that had separated out were harvested by suction filtration with Nutsche and washed with a small quantity of 30% aqueous solution of 2-propanol (the weight ratio of 2-propanol to water at completion of main crystallization was 0.43). The harvested crystals were dried in vacuo at 40° C. overnight. Analysis by high performance liquid chromatography revealed that the purity and rate of recovery of the crystal crop were 98.8% and 81%, respectively.

EXAMPLE 11

In 45 g of acetone was dissolved 10 g of a dry TOA crystal (purity 94%) obtained by the same procedure as Example 1, followed by addition of 10 g of water. Then, at 25° C., 0.1 g of TOA crystals (purity 99%) obtained by the same procedure as Example 8 were added and the system was stirred for 1 hour for preliminary crystallization. The system was further stirred at the same temperature for about 30 minutes to confirm the improvement of stirring the deposited slurry (the amount of the deposited slurry obtained by preliminary crystallization was 10% and the weight ratio of acetone to water was 4.5). For main crystallization, 58 g of water was added over 2 hours at the same temperature. The mixture was stirred at the same temperature for 30 minutes, at the end of which time the TOA crystals that had separated out were harvested by suction filtration with Nutsche and washed with a small quantity of 40% aqueous solution of acetone (the weight ratio of acetone to water at completion of main crystallization was 0.66). The harvested crystal crop was dried in vacuo at 40° C. overnight. Analysis by high performance liquid chromatography revealed that the purity and rate of recovery of the crystals were 99.0% and 84%, respectively.

EXAMPLE 12

In 40 g of acetonitrile at room temperature was dissolved 4 g of a dry TOA crystal (purity 94%) obtained by the same procedure as Example 1, followed by addition of 14 g of water. Then, at 25° C., 0.1 g of TOA crystals (purity 99%) obtained by the same procedure as Example 8 were added and the system was stirred for 1 hour for preliminary crystallization. The system was further stirred at the same temperature for about 30 minutes to confirm the improvement of stirring the deposited slurry (the amount of the deposited slurry obtained by preliminary crystallization was 8% and the weight ratio of acetonitrile to water was 2.86). For main crystallization, 146 g of water was added over 2 hours at the same temperature. The mixture was stirred at the same temperature for 30 minutes, at the end of which time the TOA crystals which had separated out were harvested by suction filtration with Nutsche and washed with a small quantity of 30% aqueous solution of acetonitrile (the weight ratio of acetonitrile to water at completion of main crystallization was 0.25). The harvested crystal crop was dried in vacuo at 40° C. overnight. Analysis by high performance liquid chromatography revealed that the purity and rate of recovery of the crystals were 99.3% and 70%, respectively.

Comparative Example 1

An aqueous solution of TOA (containing 6 g of TOA), 100 g, obtained by the same procedure as Reference Example 1 was adjusted to pH 8 with 55% sulfuric acid under stirring. Except for omitting the addition of toluene, 10% sulfuric acid was added under stirring at room temperature to adjust the solution to pH 3.0 (the addition of sulfuric acid was made over 1 hour) in the same manner as in Example 1. As a result, a yellow oil was separated out and substantially no crystal crop could be harvested by suction filtration with Nutsche, indicating that the described procedure does not yield a crystal crop that might be harvested by filtration.

Comparative Example 2

In 40 g of methanol at room temperature was dissolved 10 g of a dry TOA crystal (purity 94%) obtained by the same procedure as Example 1. When 40 g of water was continuously added over about 20 minutes under stirring at 25° C., the system became hardly stirrable in the course of crystallization, indicating that when the crystallization is carried out without omitting a preliminary crystallization, good crystals can hardly be obtained with good commercial workability.

INDUSTRIAL APPLICABILITY

In accordance with the present invention, the compound (1) of high quality can be directly obtained as crystals from the reaction mixture in a simple manner and in good yield and that the compound (1) can be purified by recrystallization to higher grade at a good recovery rate.

The invention claimed is:

1. A method for crystallization of a compound (1) of the following general formula (1):

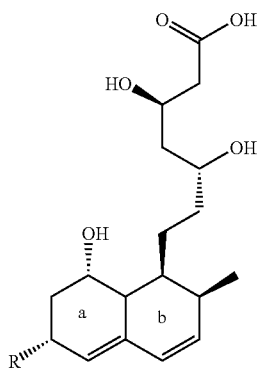

(1)

in which R is $CH_3$, $CH_2OH$, $CH_2OCOR^1$, $CO_2R^2$, $CONR^3R^4$, OH, $CH_2OR^1$ or $CH_2NR^3R^4$; $R^1$ is a $C_{1-5}$ alkyl group; $R^2$ is H or a $C_{1-5}$ alkyl group; $R^3$ and $R^4$ are independently selected from among H and $C_{1-5}$ alkyl groups; a and b each is a double bond, one of a and b is a single bond with the other being a double bond or a and b each is a single bond, which comprises acidifying a mixture of a solution of an alkali salt of the compound (1) and an organic solvent in such a manner that the solubility of the compound (1) at completion of crystallization will be 3 weight % or less and isolating the obtained crystals wherein the organic solvent to be concomitantly present is a solvent selected from among $C_{5-12}$ saturated hydrocarbons represented by $C_nH_{2n+2}$ or $C_nH_{2n}$, $C_{5-12}$ unsaturated hydrocarbons represented by $C_nH_{2n}$ or $C_nH_{2n-2}$, $C_{6-12}$ aromatic hydrocarbons, $C_{4-10}$ ethers, $C_{3-10}$ esters, $C_{3-10}$ ketones, $C_{1-8}$ halogenated hydrocarbons, $C_{2-6}$ nitriles, and $C_{1-8}$ alcohols or a mixture of two or more such solvents.

2. The method for crystallization according to claim 1, wherein the alkali salt of compound (1) is an alkali metal salt or an amine salt.

3. The method for crystallization according to claim 2, wherein the alkali metal salt is a lithium salt, a sodium salt or a potassium salt.

4. The method for crystallization according to claim 2, wherein the amine salt is an ammonium salt, a pyridinium salt, a trimethylamine salt or a triethylamine salt.

5. The method for crystallization according to claim 1, wherein the organic solvent to be concomitantly present is selected from among $C_{6-12}$ aromatic hydrocarbons.

6. The method for crystallization according to claim 1, wherein the organic solvent to be concomitantly present is a solvent selected from among pentane, n-hexane, isohexane, n-heptane, octane, methylcyclohexane, ethylcyclohexane, 1-hexene, benzene, toluene, xylene, ethylbenzene, tetrahydrofuran, 1,4-dioxane, tert-butyl methyl ether, ethyl acetate, isopropyl acetate, butyl acetate, acetone, methyl ethyl ketone, methyl isobutyl ketone, cyclohexanone, dichloromethane, 1,2-dichloroethane, acetonitrile, methanol, ethanol, 1-propanol, 2-propanol, 1-butanol, tert-butanol, 1-hexanol, and 2-hexanol or a mixture of two or more such solvents.

7. The method for crystallization according to claim 1, wherein the organic solvent to be concomitantly present is a solvent selected from among pentane, n-hexane, isohexane, n-heptane, octane, methylcyclohexane, benzene, toluene, xylene, tert-butyl methyl ether, ethyl acetate, acetone, methyl isobutyl ketone, dichloromethane, acetonitirle, and 2-propanol or a mixture of two or more such solvents.

8. The method for crystallization according to claim 1, wherein the organic solvent to be concomitantly present is a solvent selected from among benzene, toluene, and xylene or a mixture of two or more such solvents.

9. The method for crystallization according to claim 1, wherein the acidification is effected with an inorganic acid, formic acid, trifluoroacetic acid, trichloroacetic acid, p-toluenesulfonic acid, or methanesufonic acid.

10. The method for crystallization according to claim 1, wherein the acidification is effected with an inorganic acid.

11. The method for crystallization according to claim 10, wherein the inorganic acid is sulfuric acid.

12. The method for crystallization according to claim 1, wherein the acidification is effected to a final pH not higher than pH 6.

13. The method for crystallization according to claim 12, wherein the acidification is effected to a final pH not higher than pH 5.

14. The method for crystallization according to claim 12, wherein the temperature of the system at pH 6 or less is not over 70° C.

15. The method for crystallization according to claim 12, wherein the temperature of the system at pH 5 or less is 0 to 60° C.

16. The method for crystallization according claim 1, wherein the solution of an alkali salt of compound (1) is a reaction solution resulting from deacylation of a compound (2) of the following general formula (2):

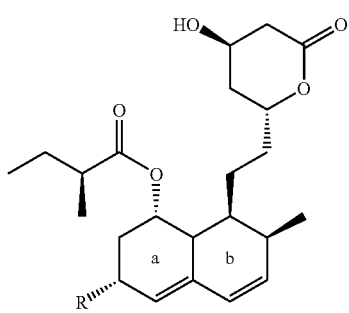
(2)

wherein R, a, and b are as defined in claim 1, or a solution obtainable by subjecting said reaction solution to concentration or solvent substitution.

17. The method for crystallization according to claim 16, wherein an impurity or color contaminant by-produced in the course of deacylation is removed with an adsorbent in advance of crystallization.

18. The method for crystallization according to claim 1, wherein R is $CH_3$ or OH.

19. The method for crystallization according to claim 1, wherein R is $CH_3$.

* * * * *